(12) United States Patent
Hudnall et al.

(10) Patent No.: US 7,348,145 B2
(45) Date of Patent: Mar. 25, 2008

(54) CLINICAL ASSAYS FOR THE DETECTION AND TYPING OF HUMAN HERPESVIRUSES

(75) Inventors: S. David Hudnall, Bellaire, TX (US); Tiansheng Chen, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 523 days.

(21) Appl. No.: 10/641,665

(22) Filed: Aug. 14, 2003

(65) Prior Publication Data

US 2004/0110195 A1 Jun. 10, 2004

Related U.S. Application Data

(60) Provisional application No. 60/403,417, filed on Aug. 14, 2002.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.31; 536/24.32; 536/24.33

(58) Field of Classification Search .................. 435/6, 435/91.2; 536/24.31, 24.32, 24.33
See application file for complete search history.

(56) References Cited

U.S. PATENT DOCUMENTS 6,958,210 B2 * 10/2005 Smith et al. .................. 435/5

FOREIGN PATENT DOCUMENTS

WO WO 9704105 A1 * 2/1997

* cited by examiner

*Primary Examiner*—Suryaprabha Chunduru
(74) *Attorney, Agent, or Firm*—Benjamin Aaron Adler

(57) ABSTRACT

The present invention provides methods of unambiguously identifying a human herpesvirus in a sample. The assays, which allow for the detection and typing of all ten human herpesviruses, involve multiplex PCR assays using consensus primers to amplify conserved regions of the herpesvirus DNA. A dot blot/chemiluminescence assay and real time PCR assay ideal for clinical setting were disclosed. A heteroduplex mobility assay suitable for uses in research laboratory was also presented.

9 Claims, 9 Drawing Sheets

CLINICAL ASSAYS FOR THE DETECTION AND TYPING OF HUMAN HERPESVIRUSES

CROSS-REFERENCE TO RELATED APPLICATIONS

This non-provisional patent application claims benefit of provisional patent application U.S. Ser. No. 60/403,417, filed Aug. 14, 2002, now abandoned.

BACKGROUND OF THE INVENTION

1. Field of the Invention

The present invention relates generally to the study of herpesviruses. More specifically, the present invention relates to clinical assays for the detection and typing of human herpesviruses.

2. Description of the Related Art

There are more than 100 known herpesviruses in the family of Herpesviridae. Of these, eight are known to infect humans. The eight human herpesviruses are herpes simplex virus 1 (HSV-1), herpes simplex virus 2 (HSV-2), varicella-zoster virus (VZV), Epstein-Barr virus (EBV), cytomegalovirus (CMV), herpesvirus 6 (HHV-6), herpesvirus 7 (HHV-7), and herpesvirus 8 (HHV-8), also known as Kaposi's sarcoma associated herpesvirus (KSHV).

Based on the length of viral replication cycle and host tissue range, the herpesviruses are classified into 3 subfamilies (alpha-, beta-, & gamma-herpesviruses, Table 1). Following primary infection, all herpesviruses establish latent persistent infections within tissues characteristic for each virus. For example, the alpha-herpesviruses HSV1, HSV2 and VZV are neurotropic, while EBV, CMV, HHV6, HHV7 and HHV8 are lymphotropic.

All herpesviruses share certain characteristics. All are composed of a core of double-stranded DNA encased within an icosahedral capsid and a phospholipid bilayer envelope. Human herpesvirus infections are very common and widely distributed. Serologic surveys indicate that >95% of adults worldwide have been infected by VZV, EBV, and HHV-6.

Despite a vigorous anti-viral immune response, herpesviruses persist in the host following primary infection. This asymptomatic latent period may be interrupted by periods of viral reactivation during which virus replicates and clinical symptoms may occur. Examples include recurrent cold sores (HSV-1), herpes zoster (shingles) in older adults arising from VZV acquired during childhood (chicken pox), CMV pneumonitis in immunocompromised organ transplant patients, and recurrent mononucleosis in patients with chronic (EBV) mononucleosis syndrome.

In many cases, the diagnosis of herpesvirus infection cannot be accurately made by clinical findings alone. Symptoms are often nonspecific, e.g. fever, malaise, lymphadenopathy, and rash. Patients can sometimes be infected with more than one herpesvirus (e.g. frequent association of HHV-8 and EBV in primary effusion lymphoma, HSV-1 and HSV-2 in orogenital ulcers). Whereas infections with the _-herpesviruses and CMV are usually amenable to acyclovir or gancyclovir anti-viral treatment, no clearly effective drug treatment is available for EBV, HHV-6, HHV-7, and HHV-8. Thus, identification of specific human herpesvirus infection is necessary before proper therapy can be selected.

The pathogenesis and clinical importance of the recently identified lymphotropic viruses HHV-6, HHV-7 and HHV-8 are not well understood. A better clinical understanding of these viruses requires the availability of appropriate diagnostic approaches for their detection and identification. All these factors, along with the worldwide impact of human herpesvirus infection, drive the need for a reliable multiplex clinical assay for the detection and identification of all eight human herpesviruses. Although a clinical assay need not differentiate EBV-1 from EBV-2 or HHV-6A from HHV-6B, it should be able to detect each variant and to distinguish all strains of EBV and HHV-6 from the other herpesviruses.

Current laboratory techniques for detection of herpesvirus infection include virus culture, viral serology, and viral DNA detection by PCR. Given the lack of optimal methods, viral culture is not generally available for detection of EBV, HHV-6, HHV-7, and HHV-8 infections. Culture detection of HSV, VZV, and CMV often suffers from poor sensitivity and very slow turn-around time. Serologic testing for HHV-6, HHV-7, and HHV-8 are not widely available, and due to their close antigenic similarity, distinction of HSV-1 from HSV-2 infection by serologic methods is often unreliable. In addition, in many cases it is difficult to serologically distinguish between acute infection and normal baseline seropositivity, thus necessitating the inconvenience of obtaining both acute and convalescent titers. Given the considerable limitations of culture and serology for herpesvirus detection, PCR detection methods have been developed. PCR offers the distinct advantages of rapid turn-around time, high sensitivity, and high specificity for the detection of herpesvirus infections.

Significant interest in the molecular evolution of herpesviruses led to sequencing of the genomes of many of the human and non-human herpesviruses. Although there are substantial differences between the genomes of different human herpesviruses, certain highly conserved regions, including the DNA polymerase gene, have been identified. This information has been utilized to develop multiplex PCR assays using consensus primers to conserved regions of the herpesvirus DNA polymerase gene.

Rozenberg and Lebon (1991) described a single step PCR assay using a consensus primer pair for HSV-1, HSV-2, EBV, and CMV, followed by typing of the amplicons by restriction fragment length polymorphism analysis (RFLP). However, the complexity of RFLP restricts its use to sophisticated laboratory environments. Moreover, the consensus primer set did not amplify VZV or HHV-6. Tenorio et al. (1993) revised this approach to include amplification of VZV, yet again typing the amplicons with RFLP. Aono et al. (1994) described a multiplex PCR using consensus primers for the detection of the three _-herpesviruses (HSV-1, HSV-2 and VZV) by virus-specific probe hybridization. Unlike restriction fragment length polymorphism, virus-specific probe hybridization is more compatible with clinical laboratory requirements of short cycle time and simplicity.

van Devanter et al. (1996) developed a set of degenerate consensus primers for PCR amplification of conserved regions of the DNA polymerase gene. The resulting nested consensus primer PCR method allowed for amplification and identification of most (14 of 15) of the animal herpesviruses and 6 of 8 human herpesviruses (HHV-1, HHV-2, VZV, EBV, CMV, HHV-6B). The method did not amplify human DNA polymerase, or yeast/mold DNA polymerase that are common contaminants of human samples. However, the methodology exhibited a wide variation in sensitivity across the human herpesviruses tested. The LOD (limit of detection) varied between 1 copy per 100 ng DNA for HSV-1 and HSV-2, and 100 copies for EBV and VZV. No data was presented on amplification of HHV-7 or HHV-8. van Devanter identified each virus by direct DNA sequencing of the amplified products obtained from an ethidium bromide stained agarose gel. This method of DNA sequence typing is a highly complex, laborious method not appropriate for use in a clinical diagnostic laboratory. Moreover, van Devanter did not demonstrate that the method could identify more than one herpesvirus in a single sample.

Ehlers et al. (1999) developed an enhanced version of the van Devanter method. Ehlers noted that the van Devanter method exhibited a wide variation in binding of the degenerate primers to different herpesviruses. Knoth et al. (1988) had previously shown that reducing primer degeneracy with deoxyinosine (dI) improved the performance in DNA amplification from related species. Ehlers thus substituted deoxyinosine (dI) at the 3- and 4-fold degenerate positions within the van Devanter primers. DNA polymerase of some herpesviruses were not amplified at all by the dI-substituted primers (e.g. CMV). Using a mixture of dI-substituted and unsubstituted primers, Ehlers found that the mixed primer set improved overall performance for herpesviruses from a range of species. Ehlers demonstrated that 6 of the 8 human herpesviruses (HSV-1, HSV-2, VZV, EBV, CMV and HHV-8) could be amplified by this method, while reducing the virus-related variability in the limit of detection. However, the important issues of assay complexity and turn-around time were not addressed since Ehlers, like van Devanter, intended to utilize the assay primarily to support research rather than clinical analysis.

Colimon et al. (1996) developed the use of "stair primers" to allow PCR amplification of viral genomes with frequent point mutations, such as HIV and hepatitis C virus. Minjolle et al. (1999) adopted the use of these "stair primers" for herpesvirus assay, utilizing mixtures of consensus stair primers to amplify DNA polymerase for the detection of 6 of the 8 human herpesviruses (HHV-1, HHV-2, VZV, EBV, CMV and HHV-6). However, the stair primer method requires 11 sets of synthetic primers. Amplicons were detected by virus-specific probe hybridization with chromogenic detection.

Robert et al. (2002) utilized a commercially available kit based on Minjolle's stair primers in a two stage multiplex PCR assay of 6 herpesviruses (HHV-1, HHV-2, VZV, EBV, CMV, and HHV-6) in tear fluid. Samples were amplified using the Argene Herpes Consensus Generic Kit. Amplicons positive for herpesvirus were typed with the Argene Herpes Identification (Hybridowell) Kit by virus-specific probe hybridization with a chromogenic substrate for detection.

Pozo and Tenorio (1999) developed a two-step consensus primer PCR assay for the 6 lymphotropic human herpesviruses. Six pairs of primers were used in a first PCR step to produce a virus-specific 194 bp amplicon of the DNA polymerase gene. Then six pairs of primers were used in a second PCR step in which the reverse primer targets a highly conserved region of each amplicon, and the forward primer governs a difference in amplicon size (e.g. 54-122 bp). Subsequent gel electrophoresis with ethidium bromide-staining allowed typing of each band by its migration rate on the gel. A limit of detection of 10-100 copies for the 6 lymphotropic herpesviruses was reported.

Johnson et al. (2000) recently developed a two-step PCR-based assay for detection and species identification of human herpesviruses. Two consensus primer pairs were used, one for the three α-herpesviruses, the other pair for the five β and γ-herpesviruses. The primer pairs bracketing a highly conserved region of the DNA polymerase gene allowed amplification of all eight major human herpesviruses at a limit of detection of 10-100 copies, with the exception of CMV that had a limit of detection of 400 copies. Johnson also claimed to be the first to differentially diagnose HHV-6A and HHV-6B variants, although this does not appear to have clinical significance. Johnson used agarose gel electrophoresis with visual identification of fluorescent ethidium bromide stained bands to identify sample amplicons positive for human herpesvirus. Positive amplicon reaction mixtures were then subjected to two separate restriction endonuclease digestions (BamHI and BstUI). The restriction digests were then subjected to agarose gel electrophoresis and the human herpesvirus species was identified based on the restriction fragment patterns (RFLP) on the two gels. However, the use of dual RFLP is overly complex and time-consuming for the clinical laboratory.

Thus, the prior art is deficient in assays capable of detecting and typing all human herpesviruses in a clinical setting. The present invention fulfills this long-standing need and desire in the art.

TABLE 1

Human Herpesviruses

| α Herpesviruses | β Herpesviruses | γ Herpesviruses |
|---|---|---|
| Short replication cycle | Long replication cycle | Very restricted host range |
| Host cell death | Host cell enlargement | Establish latent infection in lymphoid tissue (lymphotropic) |
| Replicate in broad range of host tissues | Restricted host range | |
| | Establish latent infection in many cell types (secretory glands, kidneys, epithelium, endothelium, monocytes, lymphocytes) | |
| Establish latent infection in sensory nerve ganglia (neurotropic) | | |
| HSV-1 Herpes simplex type 1 (oral herpes) | CMV (congenital infection, retinitis, pneumonitis) | EBV (EBV-1 and EBV-2 variants) Burkitt lymphoma, nasopharyngeal carcinoma, Hodgkin lymphoma, AIDS lymphoma, PTLD) |
| HSV-2 Herpes simplex type 2 (genital herpes) | HHV-6 (6A and 6B variants) (roseola, kidney transplant rejection) HHV-7 | |
| VZV (chickenpox, herpes zoster or shingles) | | HHV-8 (KSHV) Kaposi's sarcoma, primary effusion lymphoma |

SUMMARY OF THE INVENTION

There are eight currently known human herpesviruses, all of which are capable of latent persistence and reactivation following primary infection. Herpesvirus induced disease is common, widespread, and associated with significant morbidity, particularly in the immunocompromised human host. Current methods of herpesvirus detection such as viral culture and polymerase chain reaction (PCR) have limitations that need improvement.

The present invention describes robust PCR methods capable of unambiguous identification of all eight human herpesviruses, including EBV and HHV-6 subtypes, even in the presence of mixed infection. The methods are based upon amplification of the highly conserved herpesvirus DNA polymerase gene, and would provide rapid detection of human herpesviruses from human tissues and body fluid.

In one embodiment of the present invention, there is provided a dot blot/chemiluminescence assay that has test cycle time superior to both culture-based methods and PCR assay methods that rely on amplicon typing by direct sequencing or restriction fragment length polymorphism analysis (RFLP). The steps of the instant dot blot/chemiluminescence assay include sample DNA extraction, PCR, and virus-specific probe hybridization with chemiluminescent detection that require approximately 1.5 hours. All steps can be done in parallel for multiple samples, and are amenable to automation. The use of chemiluminescent detection in the final human herpesvirus identification step provides superior sensitivity and specificity compared to prior art use of virus-specific probe hybridization with chromogenic detection.

In another embodiment of the present invention, the identification assay can be carried out in the methodology of real time PCR using molecular beacon probes. Real time PCR offers the potential for viral load quantitation and avoids routine PCR contamination problems. Eight molecular beacon probes specific for each of the eight human herpesviruses have been generated herein. The entire assay (for all 8 herpesviruses) is accomplished by setting up 2 PCR reactions—each containing 4 molecular beacons labeled with 4 different fluorochromes.

The present invention also provides a method of identifying herpesviruses in a complex sample by heteroduplex mobility analysis (HMA) that uses agarose gel electrophoresis to separate homoduplex and heteroduplex bands formed by mixture of sample PCR product with herpesvirus control PCR products.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 3A. In lane 1 (HSV-1) there is only a single fast-migrating homoduplex band without any low mobility heteroduplex band in the upper region of the lane. In lane 2 (HSV-2) there is a heteroduplex band just above the homoduplex band. In all other lanes there are 1-2 slow-migrating heteroduplex bands in addition to prominent fast-migrating homoduplex bands. This result identifies the sample as HSV-1 positive. FIG. 3B. In lane 2 (HSV-2) there is only a single homoduplex band while all other lanes show slower-migrating heteroduplex bands. Lane 1 shows a fast-migrating heteroduplex band consistent with the close sequence similarity of HSV-1 with HSV-2. FIG. 3C. In lane 3 (VZV) there is a single homoduplex band, while in all other lanes there are 1-2 slower-migrating heteroduplex bands. FIG. 3D. In lane 4 (EBV) there is a single homoduplex band, while in all other lanes there are 1-2 slower-migrating heteroduplex bands. FIG. 3E. In lane 5 (CMV) there is a single homoduplex band, while in all other lanes there are 1-2 slower-migrating heteroduplex bands. FIG. 3F. In lane 6 (HHV-6) there is a single homoduplex band, while in all other lanes there are 1-2 slower-migrating heteroduplex bands. FIG. 3G. In lane 7 (HHV-7) there is a single homoduplex band, while in all other lanes there are 1-2 slower-migrating heteroduplex bands. FIG. 3H. In lane 8 (HHV-8) there is a single homoduplex band, while in all other lanes there are 1-2 slower-migrating heteroduplex bands.

FIG. 4A demonstrates HSV-1 positivity in vesicle fluid. Note identity of result in lane 1 (single homodimer) with that of lane 9, which contains unknown PCR product only. Note presence of the extra heterodimer band just above the homodimer band in lane 2 (HSV-2). FIG. 4B. HMSA of a clinical sample (KS skin biopsy) demonstrating HHV-8 positivity (lane 8). Note identity of result in lane 8 with that of lane 9 (unknown PCR product only). FIGS. 4C. Dual HMSA (HSV-1 and HSV-2). Pan-herpes PCR product of a sample containing both HSV-1 and HSV-2 DNA was co-hybridized with the 8 standard herpesvirus PCR products. Note that in lanes 1 (HSV-1) and 2 (HSV-2) there are two fast-migrating bands—a single heteroduplex band just above a single homoduplex band. In all other lanes there are 1-2 slowly-migrating heteroduplex bands and 1 fast-migrating heteroduplex band in addition to 1-2 prominent fast-migrating homoduplex bands. This result identifies the sample as containing both HSV-1 and HSV-2.

DETAILED DESCRIPTION OF THE INVENTION

An object of the present invention is to provide screening assays that can simultaneously and unambiguously identify one or more types of human herpesvirus in a clinical sample. Using a mixed primer set comprising dI-substituted and unsubstituted consensus primers to the highly conserved herpesvirus DNA polymerase gene sequence, the methods of the present invention provide optimized conditions for amplification of all eight major human herpesviruses and EBV and HHV-6 variants. Three different detection strategies were developed, namely heteroduplex mobility shift assay (HMSA), dot blot assay and real time PCR assay using molecular beacon technology. Mixed herpesvirus infections, e.g. HSV-1 & HSV-2, can be detected with all three assays. These strategies would allow for herpesvirus detection both in the clinical laboratory (dot blot assay, real time PCR assay) and in the research laboratory (heteroduplex mobility shift analysis, dot blot assay, and real time PCR assay).

Figure 2:
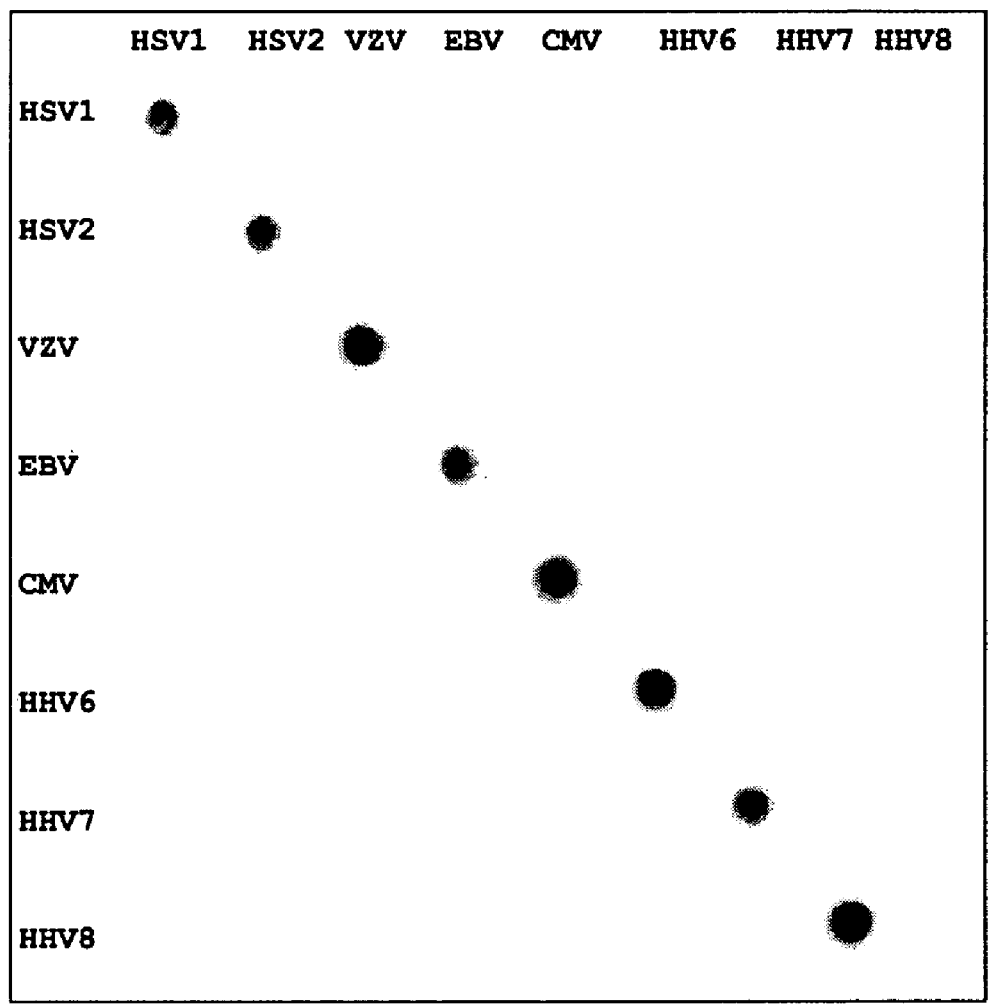
FIG. 2 shows composite photograph of 8 nylon membrane strips (arranged lengthwise), each pre-spotted with cloned herpesvirus DNA (left to right: HHV-1 to HHV-8) and hybridized with digoxigenin-labeled pan-herpes PCR products obtained from human herpesviruses 1-8 (labeled along the Y-axis). Note that a single herpesvirus DNA product is detected on each nylon strip.
Figure 3A:
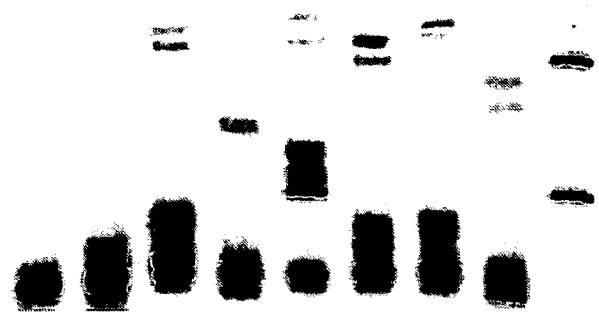
FIGS. 3A-3H shows sample pan-herpes PCR products co-hybridized with 8 standard herpesvirus PCR products [left to right: lane 1 (HSV-1), lane 2 (HSV-2), lane 3 (VZV), lane 4 (EBV), lane 5 (CMV), lane 6 (HHV-6), lane 7 (HHV-7), lane 8 (HHV-8)]. Lane 9 contains the molecular size ladder.
Figure 3B:
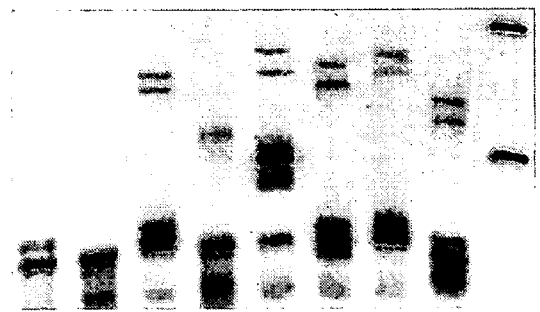
Figure 3C:
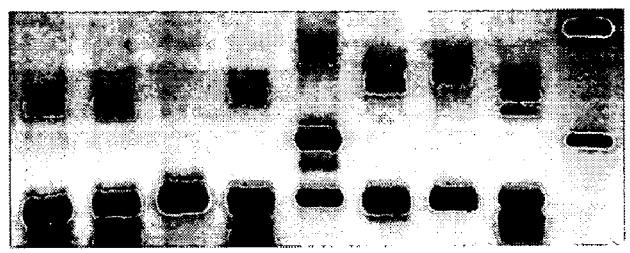
Figure 3D:
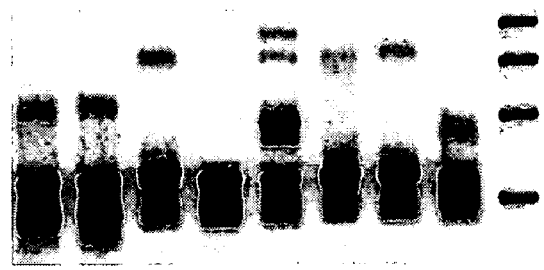
Figure 3E:
Figure 3F:
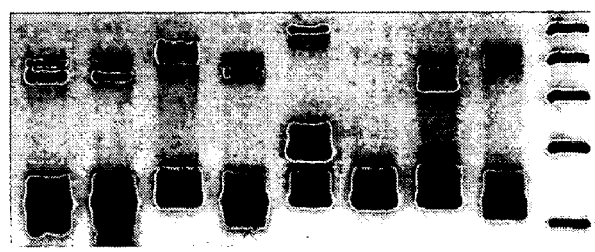
Figure 3G:
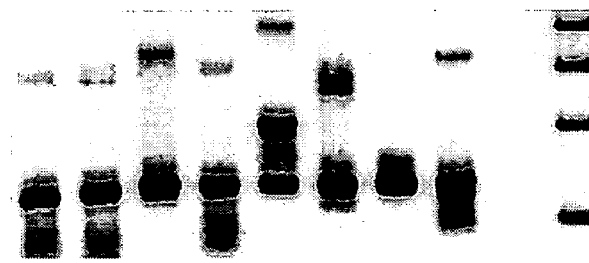
Figure 3H:
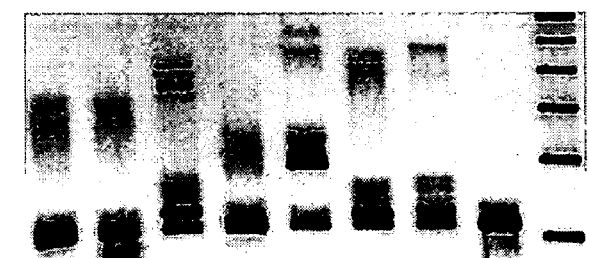

Genes sequences of DNA polymerases of each of the eight human herpesviruses were inserted into cloning vectors to produce unlimited quantities of DNA polymerase gene fragments used as standards in the assays of the present invention. In one embodiment of the present invention, there is provided a dot blot method ideal for clinical assays for herpesvirus infection. A substrate such as nylon strips are first spotted with a series of eight spots, each of which contains the consensus DNA polymerase gene fragment standard of one of the eight major human herpesviruses (FIG. 2). DNA extracted from clinical sample is subjected to single-tube herpes consensus PCR using digoxigenin-labeled nucleotides. The labeled PCR product is then applied to a test strip under conditions optimal for hybridization. Following a wash step, the strip with bound labeled viral DNA is incubated first with an alkaline phosphatase enzyme-linked anti-digoxigenin antibody, followed by a brief exposure to the chemiluminescent substrate which releases light when exposed to alkaline phosphatase. The presence of amplified herpesvirus DNA is easily detected following a short exposure of the strip to photographic film, development of which allows detection of a light-emitting spot due to PCR product bound to one of the eight herpesvirus probes. No significant cross-hybridization between herpesviruses was detected, and in no case did non-herpesviral DNA produce false positive results.

Chemiluminescent detection is highly desirable since it is easy to perform, extremely sensitive with extremely low background, non-radioactive, and not subject to fluorescent quenching problems. Thus, the dot blot-chemiluminescence assay is simple, fast, robust, sensitive (detects all eight human herpesviruses), and capable of detecting more than one herpesvirus in a single sample.

The present invention can also employ real time PCR with molecular beacon probes technology. Real time PCR detection provides further advantages in that it is faster, more sensitive and is capable of batching multiple samples. Real time PCR also offers viral load quantitation and avoids routine PCR contamination problems. A 2 tubes-8 viruses assay can be carried out as follows. Each tube contains the consensus PCR primers as well as four herpesvirus-specific molecular beacon probes that are labeled with different fluorochromes. PCR is run in a real time PCR machine that can differentially detect and quantify each herpesvirus.

Molecular beacon probe is oligonucleotide probe labeled on one end with a fluorophore and on the other end with a quencher. When the probe is not bound to target DNA, complementary sequences in the linkers on each end of the probe cause the molecular beacon to form a closed hairpin loop. As a result, the fluorochrome and the quencher are placed next to each other, rendering the probe non-fluorescent. In contrast, when the probe is bound to amplified target DNA, the fluorochrome and the quencher are separated and the probe is fluorescent.

One of ordinary skill in the art would also use TaqMan probes to detect herpesvirus in the real time PCR assay described in the present invention. TaqMan probe is a short oligonucleotide probe labeled with a reporter dye and a quencher dye that anneals to the target downstream from one of the primers. If the probe is hybridized to the target, the polymerase cleaves the hybridized probe, separating the reporter from the quencher, resulting in a higher fluorescent signal.

In another embodiment, the present invention provides a heteroduplex mobility shift assay that is more appropriate for uses in research laboratory. The heteroduplex mobility analysis uses agarose gel electrophoresis to separate heteroduplex reaction mixtures of sample amplicons and consensus DNA polymerase gene fragment standards. Following herpes consensus PCR with sample DNA, equal aliquots of the PCR samples were added to a set of 8 tubes containing each of the herpes consensus gene standards (and 1 tube with PCR sample only). After quick heating (denaturation) and cooling (annealing) steps, the mixtures were subjected to agarose gel electrophoresis followed by ethidium-bromide staining.

Heteroduplex mobility shift assay is based upon differential electrophoretic migration of DNA hybrids formed by renaturation of denatured test DNA with denatured reference DNA. The electrophoretic mobility of incompletely annealed DNA heteroduplexes formed between mismatched strands of DNA is lower than that of homoduplexes formed between matching strands. When DNA from two different herpesviruses is denatured and then renatured together, DNA heteroduplexes are formed. These heteroduplexes are seen in an ethidium bromide stained gel as slowly migrating bands, whereas homoduplexes appear as fast migrating bands. The specific identity of herpes DNA polymerase PCR product from an unknown sample is determined after examination of gel electrophoresis results of the eight mixtures with each of eight reference DNA standards (see cartoon FIG. 5A). The identity of the unknown herpesvirus is marked by absence of heteroduplexes in one lane that contains homoduplexes only (a match between unknown and standard DNA sequence).

For example, consider the heteroduplex reaction between a standard for HHV-1 and the amplicon of a sample from a patient infected with HHV-1 (thus, a "positive"). Denaturing and annealing will yield duplexes of: sense strand standard HHV-1/anti-sense strand standard HHV-1; sense strand sample HHV-1/anti-sense strand sample HHV-1; sense strand standard HHV-1/anti-sense strand sample HHV-1; and anti-sense strand standard HHV-1/sense strand sample HHV-1. Since the standard HHV-1 and sample HHV-1 are identical, the four duplexes will produce a single, intense band on the ethidium bromide-stained gel.

Now, consider the heteroduplex reaction between a standard for HHV-1 and the amplicon of a sample from a patient infected with HHV-5. Denaturing and annealing will yield hybridization of: sense strand standard HHV-1/anti-sense strand standard HHV-1; sense strand sample HHV-5/anti-sense strand sample HHV-5; sense strand standard HHV-1/anti-sense strand sample HHV-5; and anti-sense strand standard HHV-1/sense strand sample HHV-5. Depending upon their fragment lengths, the two homoduplexes may migrate either as separate bands or as a single band, while the two heteroduplexes would migrate as a somewhat broader and slower band, thus producing a pattern of two-three bands on the ethidium bromide-stained gel. When one gets to a lane where one spots the heteroduplex reaction mixture of the standard HHV-5 and the sample amplicon which is positive for HHV-5, one will then obtain a single, intense band on the ethidium bromide-stained gel. In contrast, if one considers the heteroduplex reaction between a standard for HHV-1 and the amplicon of a sample that is negative for human herpesvirus, denaturing and annealing will yield a single band in all lanes. Also, in this case, the sample control lane will show no band.

In the present invention, there is provided a method of detecting and identifying one or more types of human herpesvirus in a sample. Consensus DNA polymerase gene standards corresponding to one or more human herpesviruses are applied onto a supporting substrate. These human herpesviruses are herpes simplex virus type 1, herpes simplex virus type 2, varicella zoster virus, cytomegalovirus, human herpesvirus type 6A, human herpesvirus type 6B, human herpesvirus type 7, Epstein-Barr virus type 1, Epstein-Barr virus type 2 and human herpesvirus type 8. The supporting substrate can be nylon or nitrocellulose membrane. Representative consensus DNA standards are SEQ ID NO: 11 to 18. DNA isolated from a sample is amplified by PCR using primers of SEQ ID NO: 1 to 10 according to the PCR conditions described below. The PCR products are hybridized to the DNA on the supporting substrate and the hybridization is detected by chemiluminescent agent or molecular beacon probes. The presence of bound PCR product to a consensus DNA standard for a particular human herpesvirus would indicate the presence of said particular human herpesvirus in the sample.

In another embodiment of the present invention, there is provided a method of detecting and identifying one or more types of human herpesvirus in a sample by heteroduplex mobility analysis. DNA isolated from a sample is amplified by PCR using primers of SEQ ID NO: 1 to 10 according to the PCR conditions described below. The PCR products are hybridized to consensus DNA polymerase gene standards corresponding to one or more human herpesviruses. Representative consensus DNA standards are SEQ ID NO: 11 to 18. The hybridization products are separated by gel electorphoresis to detect the presence or absence of heteroduplexes and homoduplexes, wherein the absence of heteroduplexes after hybridizing the PCR products to a consensus DNA standard for a particular human herpesvirus indicates the presence of that particular human herpesvirus in the sample.

In yet another embodiment of the present invention, there is provided a method of detecting and identifying one or more types of human herpesvirus in a sample by real time PCR assays. DNA isolated from a sample is amplified by PCR using primers of SEQ ID NO: 1 to 10 according to the PCR conditions described below. The PCR products are detected by TaqMan probes or molecular beacon probes consisting of SEQ ID NOs: 19 to 26.

The present invention also provides a kit for the detection of one or more types of human herpesvirus in a sample. The components of the kit include a supporting substrate, consensus DNA standards, PCR primers and a chemiluminescent agent or molecular beacon probes described above. In one embodiment, a kit comprising PCR primers and consensus DNA standards SEQ ID NOs: 11, 14-16 and 18 is useful for rapid heteroduplex mobility assay.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Clinical Samples

Clinical samples include HSV-1-, HSV-2-, and VZV-positive herpetic vesicle fluids, lymph node tissues from EBV-positive Hodgkin lymphoma, peripheral blood from EBV-positive infectious mononucleosis, CMV-positive bronchoalveolar lavage fluid, skin biopsies of HHV-8-positive AIDS-associated Kaposi's sarcoma, and pleural fluid from HHV-8-positive AIDS-associated primary effusion lymphoma.

EXAMPLE 2

Pan-Herpes PCR

Herpesvirus standard DNA was obtained from the following sources; HSV-1 (clinical isolate from University of Texas Medical Branch, Galveston, Tex. (UTMB)), HSV-2 (UTMB clinical isolate), VZV (Ellen strain, ATCC, Rockville Md.), EBV (B95-8 (type 1), Jijoye (type 2), ATCC), CMV (AD169 strain, ATCC), HHV-6 (U1102 strain (type A), gift of Dr. Philip Pellett, CDC; Z-29 strain (type B), Advanced Biotechnologies, Columbia Md.), HHV-7 (H7-4 strain, Advanced Biotechnologies), and HHV-8 (BCBL-1, NIH AIDS Reagent Program, Rockville Md.).

Pan-herpes PCR is carried out as follows: 10 ng of purified standard or 0.5 ug of sample DNA was added to DNA EasyStart PCR tubes (Molecular Bioproducts) with Taq DNA polymerase (Sigma). Primers used for the PCR are shown in Table 2. First round of PCR with primers 1-4 and 7-8 was carried out as follows: 2 minutes 40 seconds at 94° C.; 55 cycles of 94° C. for 20 seconds, 46° C. for 30 seconds, 72° C. for 30 seconds; followed by 72° C. for 7 minutes. Second round of PCR with primers 5, 6, 9, 10 or primers 5 and 9 only was carried out as follows: 2 minutes 40 seconds at 94° C.; 55 cycles of 94° C. for 20 seconds, 46° C. for 20 seconds, 72° C. for 20 seconds; followed by 72° C. for 7 minutes.

Figure 1:
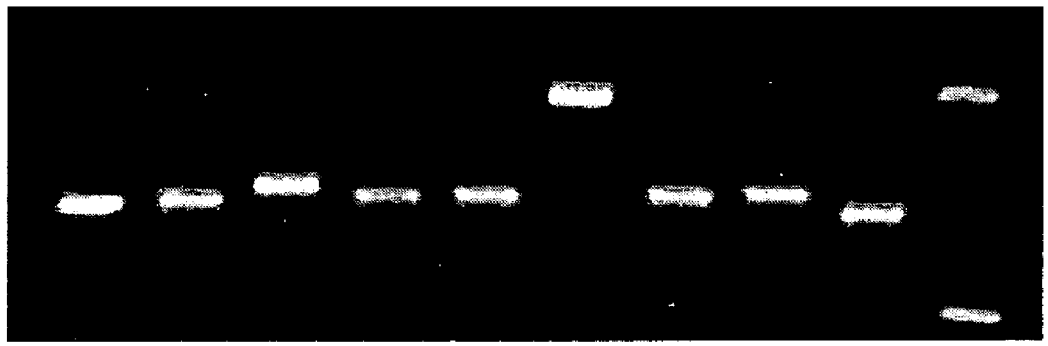
FIG. 1 shows ethidium bromide stained agarose gel of pan-herpes PCR products obtained from 9 human herpesviruses (from left to right: HSV-1, HSV-2, VZV, EBV type 1, EBV type 2, CMV, HHV-6, HHV-7, HHV-8). On the far right is a DNA molecular size ladder with DNA fragments of 300 bp and 150 bp (top to bottom). All of the products are approximately 230 bp except CMV with a molecular size of 303 bp and HHV-8 with a molecular size of 219 bp. Nucleotide sequences obtained from each of the herpesviruses are shown in Table 3.

The PCR products were loaded onto 3% Metaphor (FMC) TAE-agarose gel and electrophoresis was run for 3 hours at 125 volts (5 volts/cm). Gels are stained with ethidium bromide and viewed under UV light to demonstrate specific PCR products (see FIG. 1). All PCR products were then gel purified, sequenced (see Table 3), and confirmed by Gen-Bank BLAST searching. For dot blot hybridization, PCR is run in the presence of digoxigenin-labeled dUTP (Boehringer Mannheim, Indianapolis, Ind.) to yield digoxigenin-labeled PCR products.

TABLE 2

Herpesvirus PCR Primer Sequences

| PRIMER | SEQUENCE | SEQ ID NO |
|---|---|---|
| HERPES 1 | GAYTTYGCNAGYYTNTAYCC | 1 |
| HERPES 2 | TCCTGGACAAGCAGCARNYSGCNMTNAA | 2 |
| HERPES 3 | GAYTTYGCIAGYYTITAYCC | 3 |
| HERPES 4 | TCCTGGACAAGCAGCARIYSGCIMTIAA | 4 |
| HERPES 5 | TGTAACTCGGTGTAYGGNTTYACNGGNGT | 5 |
| HERPES 6 | TGTAACTCGGTGTAYGGITTYACIGGIGT | 6 |
| HERPES 7 | GTCTTGCTCACCAGNTCNACNCCYTT | 7 |
| HERPES 8 | GTCTTGCTCACCAGITCIACICCYTT | 8 |
| HERPES 9 | CACAGAGTCCGTRTCNCCRTADAT | 9 |
| HERPES 10 | CACAGAGTCCGTRTCICCRTAIAT | 10 |

TABLE 3

Herpesvirus PCR Product Sequences

HSV-1, 231bp (SEQ ID NO. 11)

TGTAACTCGGTGTACGGGTTCACGGGGGTGCAGCACGGACTCCTGCCGTG
CCTGCACGTTGCCGCGACGGTGACGACCATCGGCCGCGAGATGCTGCTCG
CGACCCGCAAGTACGTCCACGCGCGCTGGGCGGCCTTCGAACAGCTCCTG
GCCGATTTCCCGGAGGCGGCCGACATGCGCGCCCCCGGGCCCTATTCCAT
GCGCATCATCTACGGCGACACGGACTCTGTG
HSV-2 231bp (SEQ ID NO. 12)

TGTAACTCGGTGTACGGGTTCACGGGGGTGCAGCACGGTCTTCTGCCCTG
CCTGCACGTGGCCGCCACCGTGACGACCATCGGCCGCGAGATGCTCCTCG
CGACGCGCGCGTACATGCACGCGCGCTGGGCGGAGTTCGATCAGCTGCTG
GCCGACTTTCCGGAGGCGGCCGGCATGCGCGCCCCCGGTCCGTACTCCAT
GCGCATCATCTACGGCGACACGGACTCTGTG
VZV, 235bp (SEQ ID NO. 13)

TGTAACTCGGTGTACGGGTTCACGGGGGTTGCGCAGGGATTTCTGCCATG
TTTATACGTAGCGGCCACTGTCACTACAATTGGCCGTCAAATGTTATTAA
GTACCAGAGATTATATTCATAATAACTGGGCCGCATTTGAACGTTTTATT
ACAGCGTTTCCAGACATTGAAAGTAGCGTTCTCTCCCAAAAAGCGTACGA
GGTAAAGGTTATCTACGGCGACACGGACTCTGTG
EBV, 228bp (SEQ ID NO. 14)

TGTAACTCGGTGTACGGGTTCACGGGGGTGGCCAACGGCCTCTTTCCCTG
CCTCTCCATCGCCGAGACGGTGACGCTGCAGGGCCGCACGATGTTGGAGC
GGGCCAAGGCCTTCGTGGAGGCCCTGAGCCCCGCCAACCTGCAGGCCCTG
GCCCCTCCCCGGACGCCTGGGCGCCCCTCAACCCCGAGGGCCAGCTTCGA
GTCATCTACGGCGACACGGACTCCGTG
CMV, 303bp (SEQ ID NO. 15)

TGTAACTCGGTGTACGGGTTTACGGGGGTGGTCAACGGTATGATGCCGTG
TCTGCCCATCGCCGCCAGCATCACGCGCATCGGTCGGCACATGCTAGAGC
GCACGGCGCGGTTCATCAAAGACAACTTTTCAGAGCCGTGTTTTTTGCAC
AATTTTTTAATCAGGAAGACTATGTAGTGGGAACGCGGGAGGGGGATTCG
GAGGAGAGCAGCGCGTTACCGGAGGGGCTCGAAACATCGTCAGGGGGCTC
GAACGAACGGCGGGTGGAGGCGCGGGTCATCTATGGCGACACGGACTCTG
TG
HHV-6, 228bp (SEQ ID NO. 16)

TGTAACTCGGTGTATGGATTCACGGGGGTGGCGCACGGGTTATTGCCGTG
TGTTGCGATTGCTGCTTCTGTAACCTGTCTTGGAAGAGAGATGCTTTGTT
CCACGGTGGATTATGTTAATTCCAAGATGCAGTCCGAACAATTCTTTTGC
GAAGAATTGGGTCTAACGGCATCAGATTTTACTGGTGATTTAAAAGTGGA
GGTAATCTACGGCGACACGGACTCTGTG
HHV-7, 228bp (SEQ ID NO. 17)

TGTAACTCGGTGTATGGGTTTACGGGGGTAACACATAGCTTACTTCCATG
TGTGGCAATAGCAGCTTCTGTCACATGTCTTGGGCGTGAAATGCTTTGTA
AAACTGTTGATTACGTTGACAGCGCCATGTATTCGGACACTTTTTTCATT
GAGAAATTTGGATTGACACGCGGTGATTTTTCAGGGACATTTGGAATAGA
GGTGATCTACGGCGCCACGGACTCTGTG
HHV-8, 219bp (SEQ ID NO. 18)

TGTAACTCGGTGTATGGGTTTACGGGGGTTGCCTCTGGCATACTGCCTTG
CCTAAACATAGCGGAGACCGTGACACTACAAGGGCGAAAGATGCTGGAGA
GATCTCAGGCCTTTGTAGAGGCCATCTCGCCGGAACGCCTAGCGGGTCTC
CTGCGGAGGCCAGTAGACGTCTCACCCGACGCCCGATTCAAGGTCATCTA
CGGCGATACGGACTCTGTG

EXAMPLE 3

Preparation of Human Herpesvirus DNA Reference Clones

Amplicons obtained from each reference herpesvirus by pan-herpes PCR were cloned into the TA vector (TOPO TA cloning kit, Invitrogen). Half to two microliter PCR product, 0.5 µl 1M NaCl, and 0.5 µl vector (up to 3 µl final volume with water) were mixed and incubated at room temperature for 5 minutes. Two microliter of the mixture was then added to TOPO10 competent bacterial cells, incubated on ice for 30 minutes, and heat-shocked at 42° C. for 30 seconds. One hundred microliter of SOC was added and the suspension was shaken at 300 rpm for 1 hr at 37° C. Fifty microliters of the mixture was then spread out on ImMedia Amp Blue plates and incubated overnight at 37° C. Several white colonies were transferred into 2 ml LB broth containing ampicillin (100 µg/ml) and shaken overnight at 300 rpm at 37° C. The resulting cultures were screened for herpesvirus DNA by PCR and/or restriction fragment length analysis. Plasmids from positive cultures were then isolated, inserts removed by endonuclease digestion, and sequenced to confirm identity of each insert. The sizes of the inserts are as follows: HSV-1 & HSV-2, 231 bp; VZV, 234 bp; EBV, HHV-6, & HHV-7, 228 bp; CMV, 303 bp; and HHV-8, 219 bp.

Because HSV1 and HSV2 share very high homologous nucleotide sequence, two DNA reference clones were prepared for each virus to increase dot-blot membrane strips specificity. Primers HSVF (AGAATTCGGCCGCGAGAT-GCT, SEQ ID NO. 27) and HSVR (AGAATTCGGCCGC-CTCCGG, SEQ ID NO. 28) were specially designed for this purpose. HSVF & HSVR amplicon size was 92 bp for both HSV1 and HSV2, however 2 copies were cloned from HSV2 whereas only 1 copy from HSV1. Amplicons were purified with the QIAquick PCR purification kit, digested with EcoRI, ligated into EcoRI-digested and CIP-treated pUC18 vector, transfected into competent TOPO10 cells, and were grown and isolated as above. The PCR conditions for primers HSVF and HSVR were: 2 minutes 20 seconds at 94° C.; 40 cycles of 94° C. for 20 seconds, 55° C. for 20 seconds, 72° C. for 20 seconds; followed by 72° C. for 7 minutes.

For the same reason, two special DNA reference clones were prepared for Herpes Simplex Virus Heteroduplex Mobility Assay (See example 7). Primers HSV1F/HSV1R and HSV2F/HSV2R were for this purpose. PCRcondition for those primers: 2 minutes 40 seconds at 94° C.; 35 cycles of 94° C. for 20 seconds, 72° C. for 40 seconds; followed by 72° C. for 7 minutes. Their amplicons and related recombinant plasmids contained a 64 bp core region with the highest nucleotide sequence divergence between HSV1 and HSV2. Primers HSV1F/HSV1R and HSV2F/HSV2R were specially designed so that when their amplicons (117 bp in size using pan-herpes PCR primers 5 and 9) hybridize with those amplicons of 231 bp-insert-reference clones, two big loops were formed flanking the 64-bp core region.

Figure 7A:
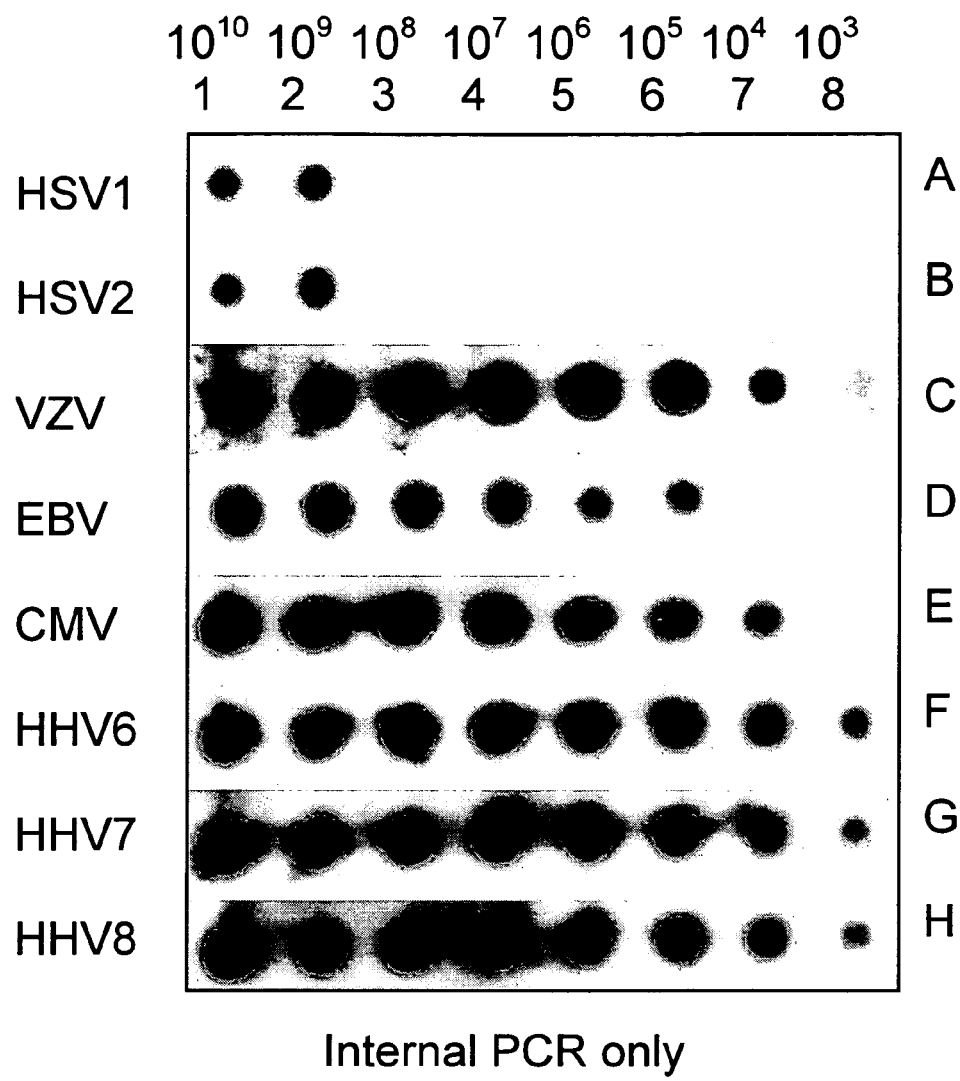
FIGS. 7A shows a pan-herpes sensitivity analysis. One internal PCR using reference clones as template DNAs which were diluted in human DNA can detect $10^3$ copies of VZV, CMV, HHV-6, HHV-7 and HHV-8 DNA molecules, $10^4$ copies of EBV DNA molecules, $10^8$ copies of HSV-1 DNA molecules and $10^9$ copies of HSV-2 DNA molecules.
Figure 7B:
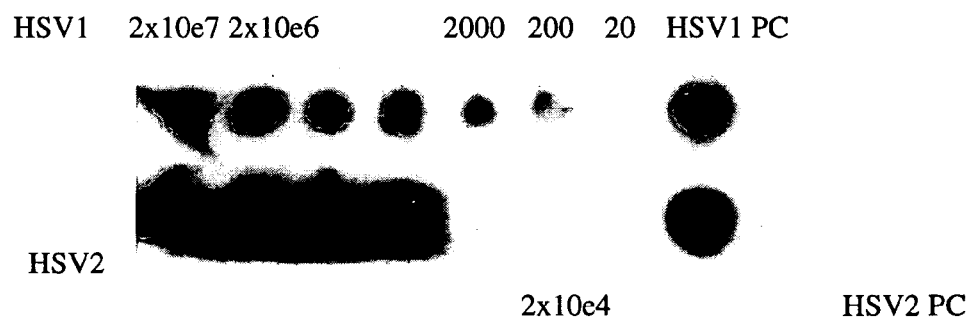
FIG. 7B shows that nested panherpes PCR can detect 200 copies of HSV-1 DNA molecules and $2 \times 10^4$ copies of HSV-2 DNA molecules. The template DNAs (external panherpes PCR products quantitated by real time PCR) were diluted in human control DNA. Each PCR reaction contains 0.5 ug human control DNA as clinical samples.

FIG. 7B shows that nested panherpes PCR can detect 200 copies of HSV-1 DNA molecules and $2 \times 10^4$ copies of HSV-2 DNA molecules.

EXAMPLE 4

Herpesvirus Species Identification by Dot Blot Assay

Nylon membrane strips (GeneScreen Plus, Dupont-NEN, Boston Mass.) for pan-herpes dot blot hybridization were prepared by applying a linear sequence of HSV-1, HHV-2, VZV, EBV, CMV, HHV-6, HHV-7, and HHV-8 recombinant reference plasmid DNA (10 ng each). Following membrane prehybridization, 10 ul of dig-labeled pan-herpes PCR product was heat denatured, mixed in 2 ml standard hybridization buffer (5×SSC, 0.1% N-lauroylsarcosine, 0.02% SDS, 1% blocking reagent), added to membrane strips, and incubated for 3 hours at 68° C. The strips were washed twice in 2×SSC, 0.1% SDS for 5 min at room temperature, and twice in 0.1×SSC, 0.1% SDS for 30 min at 68° C. The strips were next incubated with alkaline phosphatase-conjugated anti-digoxigenin antibody followed by chemiluminescent substrate according to manufacturers instructions (CSPD, Boehringer Mannheim, Indianapolis Ind.), and exposed to radiographic film (X-OMAT AR, Kodak, Rochester N.Y.) for up to 30 minutes. The identity of the PCR product was identified as a single dark spot on the film. After performing this assay on eight strips with each of the eight known herpesviruses, the strips were aligned lengthwise from top to bottom on x-ray film. As expected, one and only one herpesvirus was detected from each strip (FIG. 2). There was no cross-hybridization between herpesviruses.

Pan-herpes sensitivity analysis shows that one internal PCR using reference clones as template DNAs which were diluted in human DNA can detect $10^3$ copies of VZV, CMV, HHV-6, HHV-7 and HHV-8 DNA molecules, $10^4$ copies of EBV DNA molecules, $10^8$ copies of HSV-1 DNA molecules and $10^9$ copies of HSV-2 DNA molecules (FIG. 7A).

EXAMPLE 5

Herpesvirus Species Identification by Heteroduplex Mobility Shift Assay

Reference PCR products were prepared from the reference recombinant plasmids above by performing pan-herpes PCR (with primers 5 & 9 for 40 cycles) on 5 ng of EcoRI-digested reference plasmid. Sample PCR product was prepared from 1 ug sample DNA by performing nested pan-herpes PCR ($1^{st}$ & $2^{nd}$ rounds—55 cycles each). For each unknown sample, a series of 9 microfuge tubes each containing 3 ul of one of the eight reference PCR products (or water for negative control), 3 ul sample PCR product, 0.6 ul 10× annealing buffer (1M NaCl, 0.1M Tris pH7.8, 20 mM EDTA), and 1.4 ul 6× type 1 loading buffer (Sigma, St. Louis Mo.) was set up in small sterile microfuge tubes. The 9 mixtures were subjected to denaturation at 94° C. for 5 min, then immediately transferred to an ice-water slurry for 3 min. Each mixture was then quickly transferred to each of 9 wells of a 3% TAE-agarose gel (Metaphor, FMC Cambrex, East Rutherford N.J.) preloaded in the $10^{th}$ well with a reference DNA ladder (50-500 bp). Electrophoresis (in 1×TAE) was run for 3 hours at 125 volts (5 volts per cm). The gel was stained with ethidium bromide (0.5 ug/ml) for 30 min, destained for 30-60 min, viewed, and photographed under UV light.

Figure 4A:
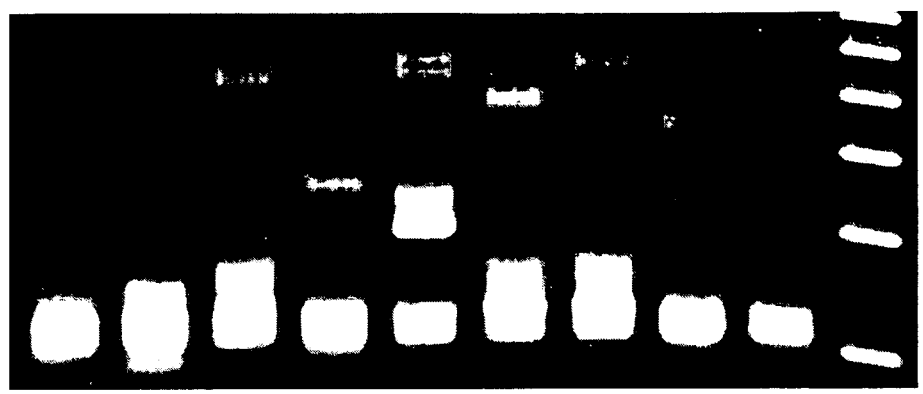
FIGS. 4A-C shows heteroduplex mobility shift assay (HMSA).
Figure 4B:
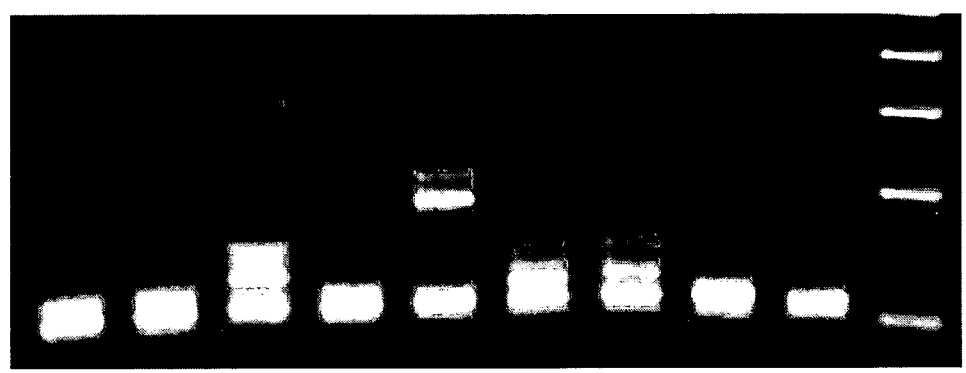
Figure 4C:
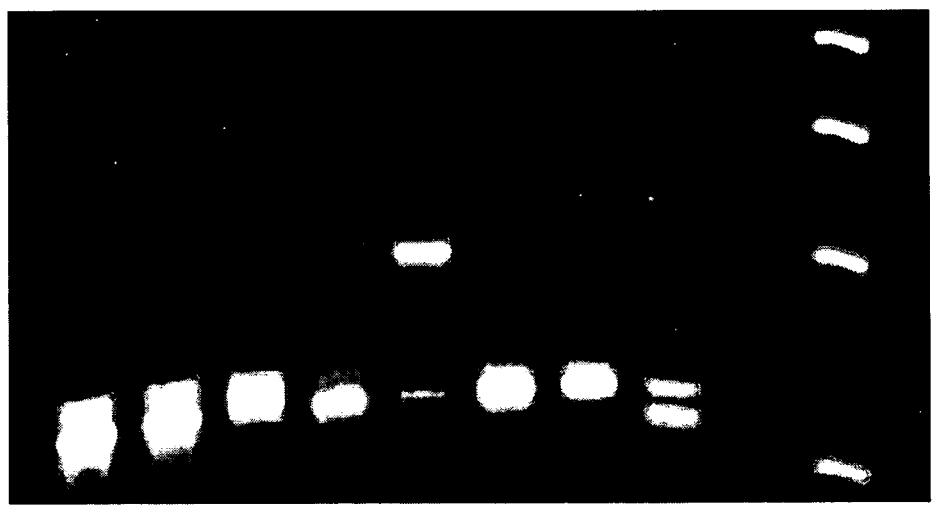

To demonstrate validity of the heteroduplex mobility shift assay (HMSA) technique, specific herpesvirus PCR products confirmed by nucleotide sequence analysis were mixed with each of the eight cloned reference PCR products in an approximate equimolar ratio. The DNA mixtures were heat-denatured and allowed to slowly reanneal to form homo- and hetero-duplexes. The eight mixtures were then subjected to agarose gel electrophoresis. After ethidium bromide staining, rapidly migrating bands representing homoduplexes and slowly migrating bands representing heteroduplexes were easily identified. A lane devoid of heteroduplexes identifies the unknown herpesvirus as matching that of the reference DNA used in that lane. With this HMSA approach, all eight human herpesviruses were unambiguously identified (FIG. 3). This assay is not only capable of detecting single herpesviruses but can also detect more than one herpesvirus in a single sample (FIG. 4).

EXAMPLE 6

Rapid Heteroduplex Mobility Assay

For rapid screening of many unknown samples, the heteroduplex mobility assay can be performed using only 3 standards (HSV-1, EBV, & HHV-6) along with a custom-made DNA ladder called 'HC' which is composed of the 219 bp HHV-8 and the 303 bp CMV reference PCR products. By simple visual analysis of the band pattern obtained, every human herpesvirus can be positively and unambiguously identified within the test sample.

Figure 5A:
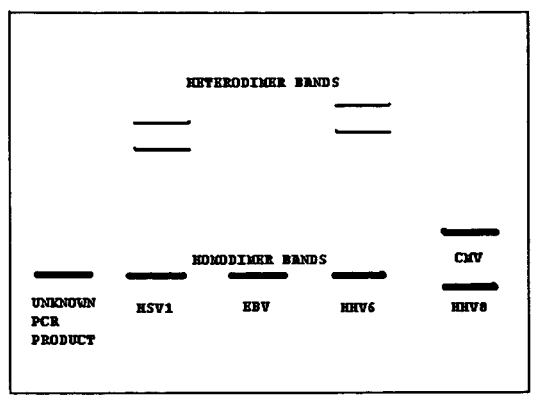
FIG. 5A shows cartoon of the HMSA Screening Assay with an EBV-positive sample. Pan-herpes PCR product from the unknown sample is co-hybridized with HSV-1, EBV, and HHV-6 DNA standards. The gel is loaded from left to right with unknown pan-herpes PCR product, unknown/HSV-1 standard mix, unknown/EBV standard mix, unknown/HHV-6 standard mix, and CMV+HHV-8 standards. Following electrophoresis, the gel is stained with ethidium bromide and photographed. Slowly-migrating heteroduplex bands are seen in the HSV-1 and HHV-6 lanes, while none are seen in the EBV lane. The size of the fast-migrating homoduplex band in the EBV lane is identical to that of the unknown itself. This result is consistent with an EBV-positive unknown.

Examples of rapid heteroduplex mobility screening assays are shown in FIG. 5. In FIG. 5A, pan-herpes PCR product from the unknown sample is mixed and hybridized with HSV-1, EBV, HHV-6 PCR products and water (which can be provided in a screening kit) to allow for homodimer and heterodimer formation. These 4 mixtures are loaded in a 3% agarose gel along with the CMV/HHV-8 PCR product mixture (which can also be provided in the kit). Slow-moving heterodimers are present with HSV1 and HHV6, indicating that the unknown is not HSV1 or HHV6. The unknown is not HSV2 or HHV7 because the slowly migrating heterodimers indicate a high degree of sequence divergence that is inconsistent with HSV2 (very similar to HSV1) or HHV7 (very similar to HHV6). The unknown PCR is also incompatible with CMV or HHV8 due to the clear difference in PCR product size (compare first lane band to last lane bands). The unknown is unambiguously Epstein-Barr virus since there are no heterodimers in the Epstein-Barr virus lane and the band size matches that of the Epstein-Barr virus homodimer.

Figure 5B:
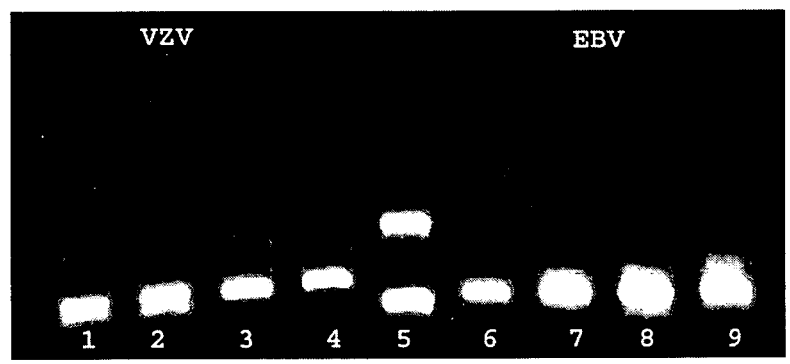
FIG. 5B shows HMSA screening for VZV and EBV. Lanes 1-3 represent VZV-positive sample PCR product with HSV-1, EBV, and HHV-6 standards, respectively. Note heteroduplex bands in all 3 lanes, demonstrating non-identity of sample with these 3 viruses as well as HSV-2. HSV-2 is excluded since the low-mobility heteroduplex bands in the HSV-1 lane are inconsistent with HSV-2. Lane 4 is sample PCR product only. Lane 5 is composed of CMV (upper band) and HHV-8 (lower band) standards. Note that the sample product size is different from CMV and HHV-8. Thus by a process of elimination the unknown is identified as VZV-positive.

FIG. 5B shows HMSA screening for VZV and EBV. Lanes 1-3 represent VZV-positive sample PCR product with HSV-1, EBV, and HHV-6 standards, respectively. Note heteroduplex bands in all 3 lanes, demonstrating non-identity of sample with these 3 viruses as well as HSV-2. HSV-2 is excluded since the low-mobility heteroduplex bands in the HSV-1 lane are inconsistent with HSV-2. Lane 4 is sample PCR product only. Lane 5 is composed of CMV (upper band) and HHV-8 (lower band) standards. Note that the sample product size is different from CMV and HHV-8. Thus by a process of elimination the unknown is identified as VZV-positive.

Figure 5C:
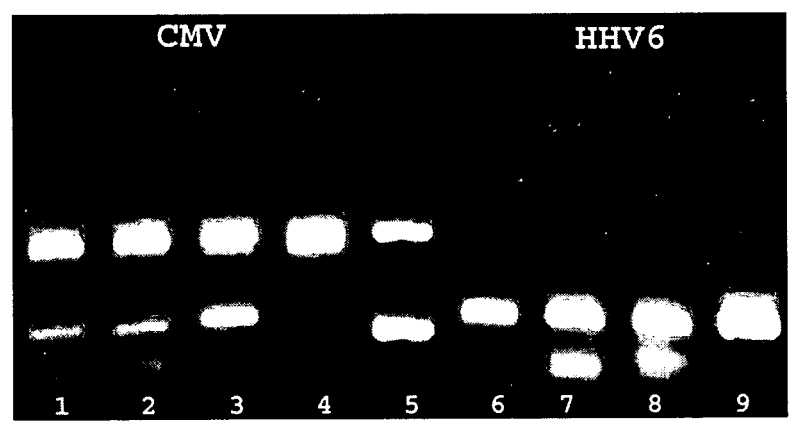
FIG. 5C shows HMSA screening for CMV and HHV-6. Lanes 1-3 represent CMV-positive sample PCR product with HSV-1, EBV, and HHV-6 standards, respectively. Note heteroduplex bands in all 3 lanes, demonstrating non-identity of sample with these 3 viruses as well as HSV-2. HSV-2 is excluded since the low-mobility heteroduplex bands in the HSV-1 lane are inconsistent with HSV-2. Lane 4 is sample PCR product only. Lane 5 is composed of CMV (upper band) and HHV-8 (lower band) standards. Note that the sample product size is identical to CMV. Thus by a process of elimination the unknown is identified as CMV-positive.
Figure 6A:
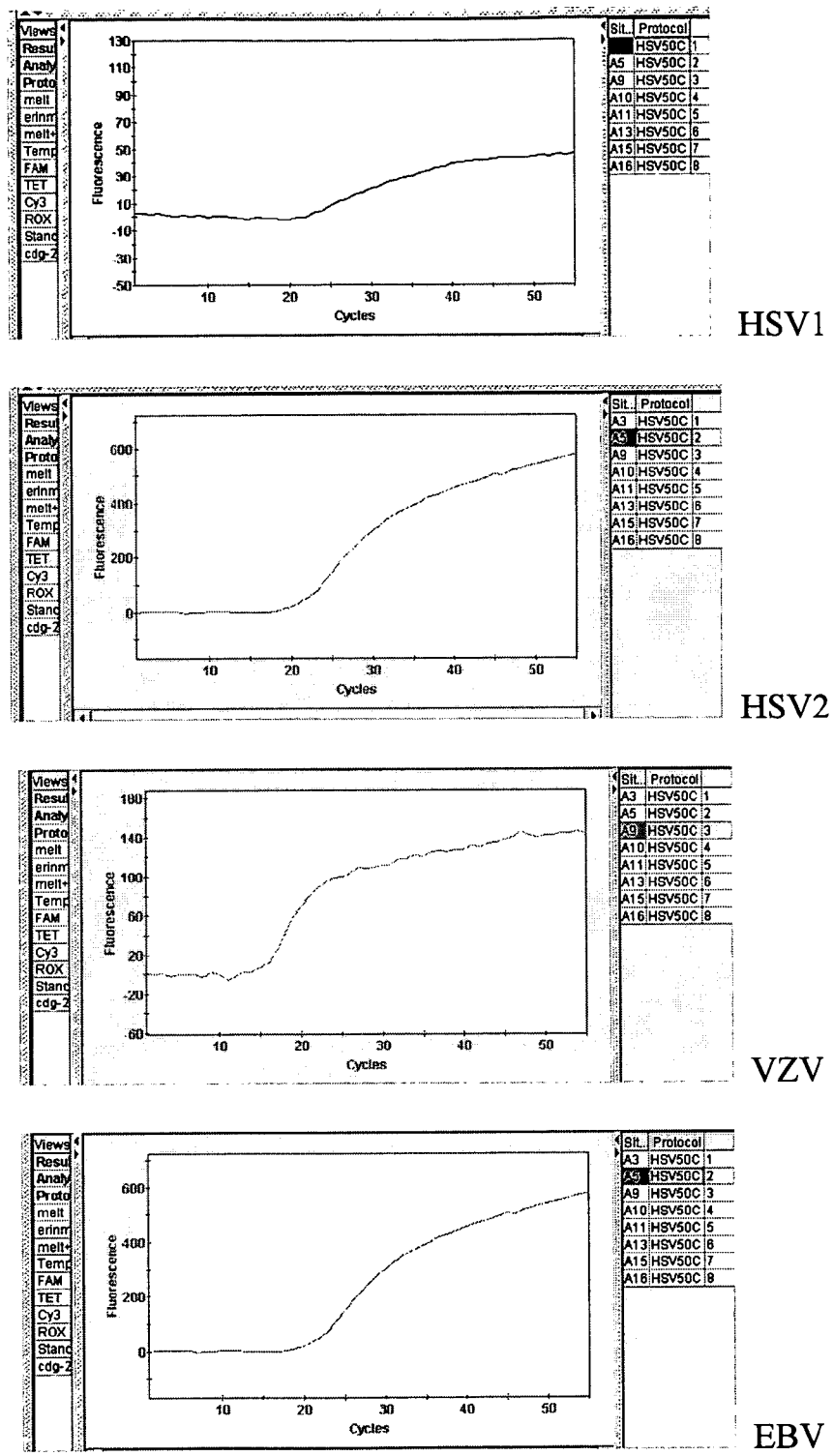
FIGS. 6A-B shows real time PCR screenshots for the 8 herpesviruses.
Figure 6B:
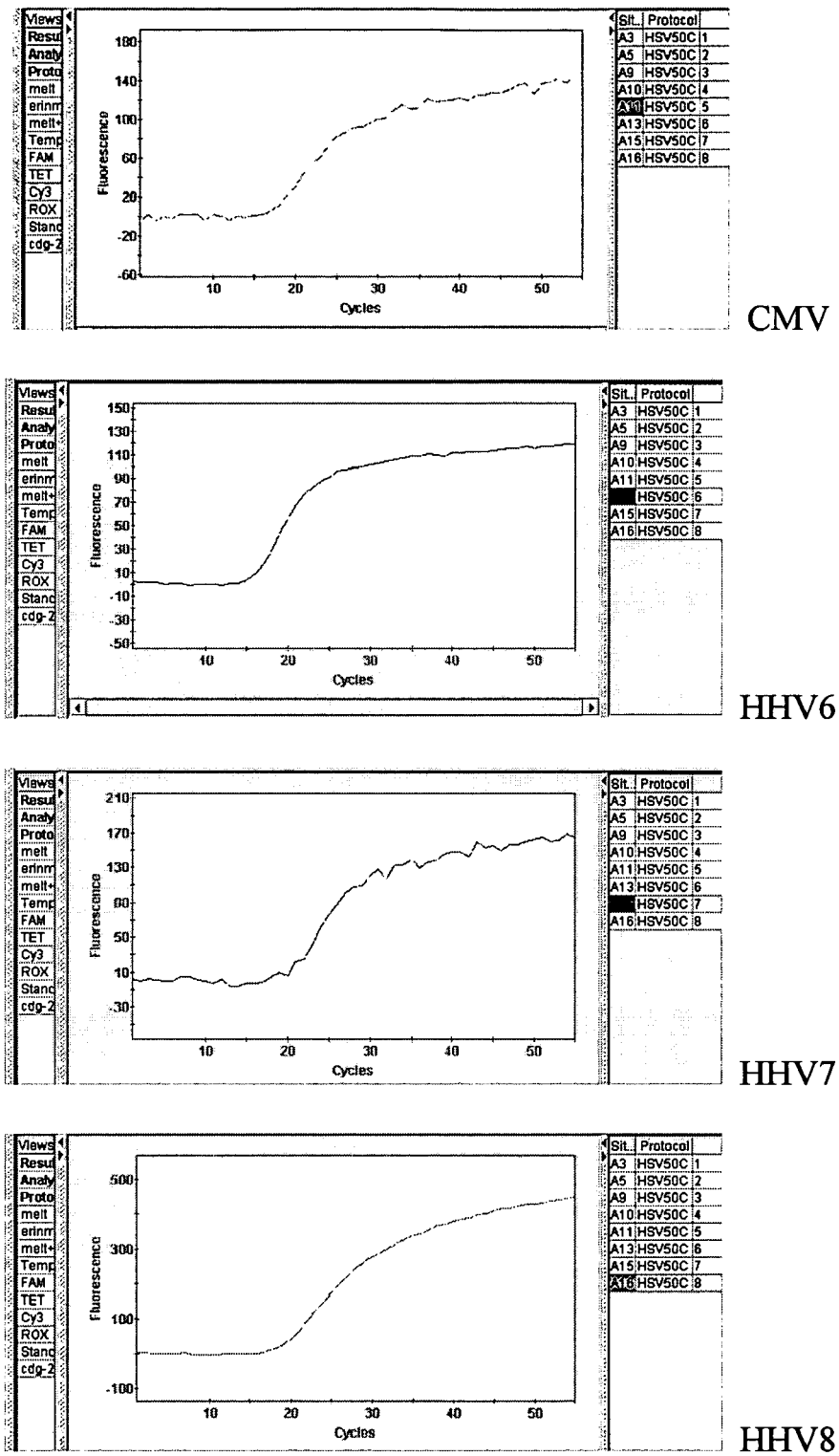

FIG. 5C shows HMSA screening for CMV and HHV-6. Lanes 1-3 represent CMV-positive sample PCR product with HSV-1, EBV, and HHV-6 standards, respectively. Note heteroduplex bands in all 3 lanes, demonstrating non-identity of sample with these 3 viruses as well as HSV-2. HSV-2 is excluded since the low-mobility heteroduplex bands in the HSV-1 lane are inconsistent with HSV-2. Lane 4 is sample PCR product only. Lane 5 is composed of CMV (upper band) and HHV-8 (lower band) standards. Note that the sample product size is identical to CMV. Thus by a process of elimination the unknown is identified as CMV-positive.

EXAMPLE 7

Herpes Simplex Virus Heteroduplex Mobility Assay

An alternative heteroduplex mobility assay procedure was designed for screening oral or genital samples suspected to be positive for either HSV-1 or HSV-2. In this assay, sample PCR product was mixed with custom-made 117 bp HSV-1 and HSV-2 standards. These standards, which include the 64 bp core region with greatest nucleotide sequence difference between HSV-1 & 2, increase the sequence difference between HSV-1 & 2 from 10% to 19% and thus increase heteroduplex mobility assay resolution and shorten optimal electrophoresis time from 3 hrs to 2 hrs. These custom standards, designed with pan-herpes primer 5 & 9 sequences flanking the 64 bp core region, bind to complimentary sequences of test sample panherpes PCR products leading the formation of two hairpin loops in each heteroduplex molecule. This unique heteroduplex structure leads to a distinctive gel mobility effect that greatly simplifies result interpretation. Samples positive for either HSV-1 or HSV-2 produce three (or four) heteroduplex mobility assay bands: one is standard DNA (117 bp), another is sample DNA (231 bp), third (and fourth) is (are) heteroduplex bands. By contrast, in standard HHV heteroduplex mobility assay (for HSV-1 & 2) in which both reference and test sample PCR products are 231 bp, the heteroduplex band may not be clearly distinct from the homoduplex band due to low resolution resulted from short electrophoresis time, low gel concentration, low quality agarose, use of TBE and/or low voltage.

EXAMPLE 8

Real Time PCR Assay

The present invention can also employ real time PCR with molecular beacon probes technology. Real time PCR detection provides further advantages in that it is faster, more sensitive and is capable of batching multiple samples. Real time PCR also offers viral load quantitation and avoids routine PCR contamination problems. A 2 tubes-8 viruses assay can be carried out as follows. Each tube contains the consensus PCR primers as well as four herpesvirus-specific molecular beacon probes that are labeled with different fluorochromes. PCR is run in a real time PCR machine that can differentially detect and quantify each herpesvirus.

For each sample, two separate PCR reactions are set up. In tube 1, sample DNA is added to molecular beacon mix FTCR1 (HSV1bcn 300 nmol/l, HSV2bcn 100 nmol/l, CMVbcn 300 nmol/l, VZVbcn 275 nmol/l) with 1× Sigma PCR buffer, 3.5 mmol/l $MgCl_2$; 0.2 mmol/l dNTP, Sigma Taq polymerase 1.5 units, and 1× additive reagent (0.2 mg/ml Bovine Serum Albumin, 150 mmol/l Trehalose and 0.2% Tween-20). In tube 2, sample DNA is added to molecular beacon mix FTCR2 (HHV6bcn 300 nmol/l, EBVbcn 100 nmol/l, HHV7bcn 300 nmol/l and HHV8bcn 200 nmol/l). Other compositions are the same in the two tubes, including 1× Sigma PCR buffer, 3.5 mmol/l $MgCl_2$; 0.2 mmol/l dNTP, Sigma Taq polymerase 1.5 units, 1× additive reagent (0.2 mg/ml Bovine Serum Albumin, 150 mmol/l Trehalose and 0.2% Tween-20), $2^{nd}$ round panherpes primers mix (SEQ ID NOs. 5, 6, 9 and 10) 1 umol/l, sample DNA or $1^{st}$ round PCR product, add $H_2O$ to 25 ul. PCR condition: 95° C., 120 seconds; 95° C., 15 seconds; 50° C., 20 seconds (optics ON), 72° C., 30 seconds, 55 cycles.

TABLE 4

Molecular Beacon Sequences

| Name | Sequence | 5' dye | 3' quencher |
|---|---|---|---|
| HSV1bcn | CCGCGTCCTTCGAACAGCTCCTGGCCGATTTCACGCGG (SEQ ID NO. 19) | 6-FAM | DABCYL |
| HSV2bcn | CCGCGAGTTCGATCAGCTGCTGGCCGACTTTCGCGG (SEQ ID NO. 20) | TET | DABCYL |
| VZVbcn | CTCGCGCTGGGCCGCATTTGAACGTTTTATTACCGCGAG (SEQ ID NO. 21) | ROX | DABCYL |
| EBVbcn | CCGGCAACGGCCTCTTTCCCTGCCTCTCCATGCCGG (SEQ ID NO. 22) | TET | DABCYL |
| CMVbcn | CCCAGGCACGGCGCGGTTCATCAAAGACAACCTGGG (SEQ ID NO. 23) | Cy3 | DABCYL |
| HHV6bcn | CCCGGAAGAGAGATGCTTTGTTCCACGGTGGACCGGG (SEQ ID NO. 24) | 6-FAM | DABCYL |
| HHV7bcn | CCGCGACGTTGACAGCGCCATGTATTCGGACATCGCGG (SEQ ID NO. 25) | Cy3 | DABCYL |
| HHV8bcn | CGCGTCATACTGCCTTGCCTAAACATAGCGGAGACGCG (SEQ ID NO. 26) | ROX | DABCYL |

The Following References were Cited herein:

Aono et al., 1994. Detection of human alpha-herpesvirus DNA using consensus primers and specific probes. Acta Otolaryngol Suppl. 514:132-134.

Colimon et al., 1996. New types of primers (stair primers) for PCR amplification of the variable V3 region of the human immunodeficiency virus. J Virol Methods 58:7-19.

Ehlers et al., 1999. Detection of new DNA Polymerase genes of known and potentially novel herpesviruses by PCR with degenerate and deoxyinosine-substituted primers. Virus Genes 18:211-220.

Johnson et al., 2000. Comprehensive PCR-based assay for detection and species identification of human herpesviruses. J Clin Microbiol. 38:3274-3279.

Knoth et al., 1988. Highly degenerate, inosine-containing primers specifically amplify rare cDNA using the polymerase chain reaction. Nucleic Acids Res. 16:10932.

Minjolle et al., 1999. Amplification of the six major human herpesviruses from cerebrospinal fluid by a single PCR. J Clin Microbiol. 37:950-953.

Pozo and Tenorio, 1999. Detection and typing of lymphotropic herpesviruses by multiplex polymerase chain reaction. J Virol Methods 79:9-19.

Robert et al., 2002. Multiplex detection of herpesviruses in tear fluid using the "stair primers" PCR method: prospective study of 93 patients. J Med Virol. 66:506-511.

Rozenberg and Lebon, 1991. Amplification and characterization of herpesvirus DNA in cerebrospinal fluid from patients with acute encephalitis. J Clin Microbiol. 29:2412-2417.

Tenorio et al., 1993. Detection and typing of human herpesviruses by multiplex polymerase chain reaction. J Virol Methods 44:261-269.

Van Devanter et al., 1996. Detection and analysis of diverse herpesviral species by consensus primer PCR. J. Clin Microbiol. 34:1666-1671.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of detecting and identifying one or more types of human herpesvirus in a sample, comprising the steps of:
   (a) applying onto a supporting substrate consensus DNA polymerase gene standards corresponding to one or more human herpesviruses;
   (b) isolating DNA from said sample;
   (c) amplifying said DNA by a nested pan-herpes PCR with a first round primer pair consisting of SEQ ID NOs: 1 and 2; and a second round primer pair consisting of SEQ ID NOS: 5 and 9 amplifying the PCR product of the first round thereby forming second round PCR products;
   (d) hybridizing said second round PCR products to said supporting substrate; and
   (e) detecting bound PCR products on said supporting substrate, wherein the presence of bound PCR product to a consensus DNA standard for a human herpesvirus indicates the presence of said human herpesvirus in said sample.

2. The method of claim 1, wherein said supporting substrate is selected from the group consisting of nylon, nitrocellulose membrane and microtiter plate.

3. The method of claim 1, wherein said consensus DNA standards are SEQ ID NOS: 11 to 18.

4. The method of claim 1, wherein said human herpesviruses are herpes simplex virus type 1, herpes simplex virus type 2, varicella zoster virus, cytomegalovirus, human herpesvirus type 6A, human herpesvirus type 6B, human herpesvirus type 7, Epstein-Barr virus type 1, Epstein-Barr virus type 2 or human herpesvirus type 8.

5. The method of claim 1, wherein said detection of bound PCR products is by chemiluminescent method.

6. A method of detecting and identifying one or more types of human herpesvirus in a sample, comprising the steps of:
   (a) isolating DNA from a sample;
   (b) amplifying said DNA by a nested pan-herpes PCR with a first round primer pair consisting of SEQ ID NOs: 1 and 2; and a second round primer pair consisting of SEQ ID NOS: 5 and 9 amplifying the PCR product of the first round thereby forming second round PCR products;
   (c) hybridizing said second round PCR products to consensus DNA polymerase gene standards corresponding to the human herpesviruses, thereby generating hybridization products; and
   (e) separating said hybridization products to detect the presence or absence of heteroduplexes and homoduplexes, wherein the absence of heteroduplexes from hybridizing said PCR products to a consensus DNA standard for a particular human herpesvirus indicates the presence of said particular human herpesvirus in said sample.

7. The method of claim 6, wherein said consensus DNA standards are SEQ ID NOS: 11 to 18.

8. The method of claim 6, wherein said human herpesviruses are herpes simplex virus type 1, herpes simplex virus type 2, varicella zoster virus, cytomegalovirus, human herpesvirus type 6A, human herpesvirus type 6B, human herpesvirus type 7, Epstein-Barr virus type 1, Epstein-Barr virus type 2 or human herpesvirus type 8.

9. A method of detecting and identifying one or more types of human herpesvirus in a sample, comprising the steps of:
   (a) isolating DNA from said sample; and
   (b) amplifying said isolated DNA by a round of PCR with a primer pair consisting of SEQ ID NOs: 1 and 2 in the presence of molecular beacon probes consisting of SEQ ID NOS: 19 to 26 each of which is specific for a human herpesvirus; wherein fluorescence signaling upon probe-specific annealing to the amplified DNA detects and identifies the presence of the specific human herpesvirus(es) within the sample using real-time PCR.

* * * * *

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<221> NAME/KEY: primer_bind
<222> LOCATION: n = any at pos 9, 15;
      y = t or c at pos 3, 6, 13, 14, 18
<223> OTHER INFORMATION: herpesvirus PCR primer

<400> SEQUENCE: 1
gayttygcna gyytntaycc                                              20

<210> SEQ ID NO 2
<211> LENGTH: 28
<212> TYPE: DNA
<213> ORGANISM: Artificial Sequence
<220> FEATURE:
<221> NAME/KEY: primer_bind
<222> LOCATION: m = a or c at pos 24; n = any at pos 18, 23,
      26; r = g or a at pos 17; s = g or c at pos 20;
      y = t or c at pos 19
<223> OTHER INFORMATION: herpesvirus PCR primer 2

<400> SEQUENCE: 2
tcctggacaa gcagcarnys gcnmtnaa                                     28

<210> SEQ ID NO 3
<211> LENGTH: 20
<212> TYPE: DNA
<213> ORGANISM: Artificial Sequence
```

-continued

```
<220> FEATURE:
<221> NAME/KEY: primer_bind
<222> LOCATION: n = deoxyinosine at pos 9, 15; y = t or c at pos 3,
      6, 12, 13, 18
<223> OTHER INFORMATION: herpesvirus PCR primer 3

<400> SEQUENCE: 3
gayttygcna gyytntaycc                                              20

<210> SEQ ID NO 4
<211> LENGTH: 28
<212> TYPE: DNA
<213> ORGANISM: Artificial Sequence
<220> FEATURE:
<221> NAME/KEY: primer_bind
<222> LOCATION: n = deoxyinosine at pos 18, 23, 26; m = a
      or c at pos 24; r = g or a at pos 17; s = g or
      c at pos 20; y = t or c at pos 19
<223> OTHER INFORMATION: herpesvirus PCR primer 4

<400> SEQUENCE: 4
tcctggacaa gcagcarnys gcnmtnaa                                     28

<210> SEQ ID NO 5
<211> LENGTH: 29
<212> TYPE: DNA
<213> ORGANISM: Artificial Sequence
<220> FEATURE:
<221> NAME/KEY: primer_bind
<222> LOCATION: n = any at pos 18, 24, 27; y = t or c at pos
      15, 21
<223> OTHER INFORMATION: herpesvirus PCR primer 5

<400> SEQUENCE: 5
tgtaactcgg tgtayggntt yacnggngt                                    29

<210> SEQ ID NO 6
<211> LENGTH: 29
<212> TYPE: DNA
<213> ORGANISM: Artificial Sequence
<220> FEATURE:
<221> NAME/KEY: primer_bind
<222> LOCATION: n = deoxyinosine at pos 18, 24, 27;
      y = t or c at pos 15, 21
<223> OTHER INFORMATION: herpesvirus PCR primer 6

<400> SEQUENCE: 6
tgtaactcgg tgtayggntt yacnggngt                                    29

<210> SEQ ID NO 7
<211> LENGTH: 26
<212> TYPE: DNA
<213> ORGANISM: Artificial Sequence
<220> FEATURE:
<221> NAME/KEY: primer_bind
<222> LOCATION: n = any at pos 15, 18, 21; y = t or c
      at pos 24
<223> OTHER INFORMATION: herpesvirus PCR primer 7

<400> SEQUENCE: 7
gtcttgctca ccagntcnac nccytt                                       26

<210> SEQ ID NO 8
<211> LENGTH: 26
<212> TYPE: DNA
<213> ORGANISM: Artificial Sequence
<220> FEATURE:
<221> NAME/KEY: primer_bind
<222> LOCATION: n = deoxyinosine at pos 15, 18, 21; y = t or
``` c at pos 24
<223> OTHER INFORMATION: herpesvirus PCR primer 8

<400> SEQUENCE: 8
gtcttgctca ccagntcnac nccytt                                          26

<210> SEQ ID NO 9
<211> LENGTH: 24
<212> TYPE: DNA
<213> ORGANISM: Artificial Sequence
<220> FEATURE:
<221> NAME/KEY: primer_bind
<222> LOCATION: n = any at pos 16; r = g or a at pos 13, 19
<223> OTHER INFORMATION: herpesvirus PCR primer 9

<400> SEQUENCE: 9
cacagagtcc gtrtcnccrt adat                                            24

<210> SEQ ID NO 10
<211> LENGTH: 24
<212> TYPE: DNA
<213> ORGANISM: Artificial Sequence
<220> FEATURE:
<221> NAME/KEY: primer_bind
<222> LOCATION: n = deoxyinosine at pos 16, 22; r = g
       or a at pos 13, 19
<223> OTHER INFORMATION: herpesvirus PCR primer 10

<400> SEQUENCE: 10
cacagagtcc gtrtcnccrt anat                                            24

<210> SEQ ID NO 11
<211> LENGTH: 231
<212> TYPE: DNA
<213> ORGANISM: Unknown
<220> FEATURE:
<223> OTHER INFORMATION: herpesvirus DNA standard for human HSV-1

<400> SEQUENCE: 11
tgtaactcgg tgtacgggtt cacggggtg cagcacggac tcctgccgtg                 50
cctgcacgtt gccgcgacgg tgacgaccat cggccgcgag atgctgctcg                100
cgacccgcaa gtacgtccac gcgcgctggg cggccttcga acagctcctg                150
gccgatttcc cggaggcggc cgacatgcgc gcccccgggc cctattccat                200
gcgcatcatc tacggcgaca cggactctgt g                                    231

<210> SEQ ID NO 12
<211> LENGTH: 231
<212> TYPE: DNA
<213> ORGANISM: Unknown
<220> FEATURE:
<223> OTHER INFORMATION: herpesvirus DNA standard for human HSV-2

<400> SEQUENCE: 12
tgtaactcgg tgtacgggtt cacggggtg cagcacggtc ttctgccctg                 50
cctgcacgtg gccgccaccg tgacgaccat cggccgcgag atgctcctcg                100
cgacgcgcgc gtacatgcac gcgcgctggg cggagttcga tcagctgctg                150
gccgactttc cggaggcggc cggcatgcgc gcccccggtc cgtactccat                200
gcgcatcatc tacggcgaca cggactctgt g                                    231

<210> SEQ ID NO 13
<211> LENGTH: 234

-continued

<212> TYPE: DNA
<213> ORGANISM: Unknown
<220> FEATURE:
<223> OTHER INFORMATION: herpesvirus DNA standard for human VZV

<400> SEQUENCE: 13
tgtaactcgg tgtacgggtt cacgggggtt gcgcagggat ttctgccatg 50
tttatacgta gcggccactg tcactacaat tggccgtcaa atgttattaa 100
gtaccagaga ttatattcat aataactggg ccgcatttga acgttttatt 150
acagcgtttc cagacattga aagtagcgtt ctctcccaaa aagcgtacga 200
ggtaaaggtt atctacggcg acacggactc tgtg 234

<210> SEQ ID NO 14
<211> LENGTH: 228
<212> TYPE: DNA
<213> ORGANISM: Unknown
<220> FEATURE:
<223> OTHER INFORMATION: herpesvirus DNA standard for human EBV

<400> SEQUENCE: 14
tgtaactcgg tgtacgggtt cacgggggtg gccaacggcc tctttccctg 50
cctctccatc gccgagacgg tgacgctgca gggccgcacg atgttggagc 100
gggccaaggc cttcgtggag gccctgagcc ccgccaacct gcaggccctg 150
gccccctccc cggacgcctg ggcgcccctc aaccccgagg gccagcttcg 200
agtcatctac ggcgacacgg actccgtg 228

<210> SEQ ID NO 15
<211> LENGTH: 303
<212> TYPE: DNA
<213> ORGANISM: Unknown
<220> FEATURE:
<223> OTHER INFORMATION: herpesvirus DNA standard for human CMV

<400> SEQUENCE: 15
tgtaactcgg tgtacgggtt tacgggggtg gtcaacggta tgatgccgtg 50
tctgcccatc gccgccagca tcacgcgcat cggtcgcgac atgctagagc 100
gcacggcgcg gttcatcaaa gacaactttt cagagccgtg ttttttgcac 150 aatttttta atcaggaaga ctatgtagtg ggaacgcggg agggggattc 200
ggaggagagc agcgcgttac cggaggggct cgaaacatcg tcagggggct 250
cgaacgaacg gcgggtggag gcgcgggtca tctatggcga cacggactct 300
gtg 303

<210> SEQ ID NO 16
<211> LENGTH: 228
<212> TYPE: DNA
<213> ORGANISM: Unknown
<220> FEATURE:
<223> OTHER INFORMATION: herpesvirus DNA standard for human HHV-6

<400> SEQUENCE: 16
tgtaactcgg tgtatggatt cacgggggtg gcgcacgggt tattgccgtg 50
tgttgcgatt gctgcttctg taacctgtct tggaagagag atgctttgtt 100
ccacggtgga ttatgttaat tccaagatgc agtccgaaca attcttttgc 150
gaagaattgg gtctaacggc atcagatttt actggtgatt taaaagtgga 200

```
ggtaatctac ggcgacacgg actctgtg                                            228

<210> SEQ ID NO 17
<211> LENGTH: 228
<212> TYPE: DNA
<213> ORGANISM: Unknown
<220> FEATURE:
<223> OTHER INFORMATION: herpesvirus DNA standard for human HHV-7

<400> SEQUENCE: 17
tgtaactcgg tgtatgggtt tacggggta acacatagct tacttccatg                      50
tgtggcaata gcagcttctg tcacatgtct gggcgtgaa atgctttgta                     100 aaactgttga ttacgttgac agcgccatgt attcggacac ttttttcatt                    150
gagaaatttg gattgacacg cggtgatttt tcagggacat ttggaataga                    200
ggtgatctac ggcgccacgg actctgtg                                            228

<210> SEQ ID NO 18
<211> LENGTH: 219
<212> TYPE: DNA
<213> ORGANISM: Unknown
<220> FEATURE:
<223> OTHER INFORMATION: herpesvirus DNA standard for human HHV-8

<400> SEQUENCE: 18
tgtaactcgg tgtatgggtt tacggggtt gcctctggca tactgccttg                      50
cctaaacata gcggagaccg tgacactaca agggcgaaag atgctggaga                    100
gatctcaggc ctttgtagag gccatctcgc cggaacgcct agcgggtctc                    150
ctgcggaggc cagtagacgt ctcacccgac gcccgattca aggtcatcta                    200
cggcgatacg gactctgtg                                                      219

<210> SEQ ID NO 19
<211> LENGTH: 38
<212> TYPE: DNA
<213> ORGANISM: Artificial Sequence
<220> FEATURE:
<221> NAME/KEY: primer_bind
<223> OTHER INFORMATION: Molecular Beacon Sequences HSV1bcn

<400> SEQUENCE: 19
ccgcgtcctt cgaacagctc ctggccgatt tcacgcgg                                  38

<210> SEQ ID NO 20
<211> LENGTH: 36
<212> TYPE: DNA
<213> ORGANISM: Artificial Sequence
<220> FEATURE:
<221> NAME/KEY: primer_bind
<223> OTHER INFORMATION: Molecular Beacon Sequences HSV2bcn

<400> SEQUENCE: 20
ccgcgagttc gatcagctgc tggccgactt tcgcgg                                    36

<210> SEQ ID NO 21
<211> LENGTH: 39
<212> TYPE: DNA
<213> ORGANISM: Artificial Sequence
<220> FEATURE:
<221> NAME/KEY: primer_bind
<223> OTHER INFORMATION: Molecular Beacon Sequences VZVbcn

<400> SEQUENCE: 21
```
ctcgcgctgg gccgcatttg aacgttttat taccgcgag          39

<210> SEQ ID NO 22
<211> LENGTH: 36
<212> TYPE: DNA
<213> ORGANISM: Artificial Sequence
<220> FEATURE:
<221> NAME/KEY: primer_bind
<223> OTHER INFORMATION: Molecular Beacon Sequences EBVbcn

<400> SEQUENCE: 22
ccggcaacgg cctctttccc tgcctctcca tgccgg             36

<210> SEQ ID NO 23
<211> LENGTH: 36
<212> TYPE: DNA
<213> ORGANISM: Artificial Sequence
<220> FEATURE:
<221> NAME/KEY: primer_bind
<223> OTHER INFORMATION: Molecular Beacon Sequences CMVbcn

<400> SEQUENCE: 23
cccaggcacg gcgcggttca tcaaagacaa cctggg             36

<210> SEQ ID NO 24
<211> LENGTH: 37
<212> TYPE: DNA
<213> ORGANISM: Artificial Sequence
<220> FEATURE:
<221> NAME/KEY: primer_bind
<223> OTHER INFORMATION: Molecular Beacon Sequences HHV6bcn

<400> SEQUENCE: 24
cccggaagag agatgctttg ttccacggtg gaccggg            37

<210> SEQ ID NO 25
<211> LENGTH: 38
<212> TYPE: DNA
<213> ORGANISM: Artificial Sequence
<220> FEATURE:
<221> NAME/KEY: primer_bind
<223> OTHER INFORMATION: Molecular Beacon Sequences HHV7bcn

<400> SEQUENCE: 25
ccgcgacgtt gacagcgcca tgtattcgga catcgcgg           38

<210> SEQ ID NO 26
<211> LENGTH: 38
<212> TYPE: DNA
<213> ORGANISM: Artificial Sequence
<220> FEATURE:
<221> NAME/KEY: primer_bind
<223> OTHER INFORMATION: Molecular Beacon Sequences HHV8bcn

<400> SEQUENCE: 26
cgcgtcatac tgccttgcct aaacatagcg gagacgcg           38

<210> SEQ ID NO 27
<211> LENGTH: 21
<212> TYPE: DNA
<213> ORGANISM: Artificial Sequence
<220> FEATURE:
<221> NAME/KEY: primer_bind
<223> OTHER INFORMATION: Primers  HSVF

<400> SEQUENCE: 27
agaattcggc cgcgagatgc t                             21

```
<210> SEQ ID NO 28
<211> LENGTH: 19
<212> TYPE: DNA
<213> ORGANISM: Artificial Sequence
<220> FEATURE:
<221> NAME/KEY: primer_bind
<223> OTHER INFORMATION: Primers  HSVR

<400> SEQUENCE: 28
agaattcggc cgcctccgg                                                  19
```